(12) United States Patent
Eicoff

(10) Patent No.: US 7,070,603 B2
(45) Date of Patent: Jul. 4, 2006

(54) EAR CLEANING APPARATUS, TIP AND A METHOD FOR CLEANING AN EAR

(75) Inventor: Jeffrey A. Eicoff, Mundelein, IL (US)

(73) Assignee: U.S. Premier Marketing, Inc., Mundelein, IL (US)

( * ) Notice: Subject to any disclaimer, the term of this patent is extended or adjusted under 35 U.S.C. 154(b) by 394 days.

(21) Appl. No.: 10/104,456

(22) Filed: Mar. 22, 2002

(65) Prior Publication Data

US 2003/0181933 A1  Sep. 25, 2003

(51) Int. Cl.
A61F 11/00 (2006.01)

(52) U.S. Cl. .................................... 606/162

(58) Field of Classification Search ............... 601/139, 601/141; 604/1; 132/317, 318; 606/162
See application file for complete search history.

(56) References Cited

U.S. PATENT DOCUMENTS

| | | | |
|---|---|---|---|
| 102,351 A | 4/1870 | Wood | |
| 147,660 A | 2/1874 | Leiner | |
| 320,889 A | 6/1885 | Ruoff | |
| 1,381,829 A * | 6/1921 | Hartman | 606/162 |
| 1,980,826 A * | 11/1934 | Reiss | 606/161 |
| 3,203,418 A | 8/1965 | Johnston | |
| 3,254,356 A * | 6/1966 | Yao et al. | 606/161 |
| 3,626,946 A | 12/1971 | Messey | |
| 5,374,276 A | 12/1994 | Lay | |
| 5,509,921 A * | 4/1996 | Karell | 606/162 |
| 5,632,756 A | 5/1997 | Kruglick | |
| 5,711,759 A * | 1/1998 | Smith et al. | 601/139 |
| 5,715,850 A * | 2/1998 | Markgraaf | 606/162 |
| 5,807,301 A | 9/1998 | Nadam | |
| 5,846,215 A * | 12/1998 | Zygmont | 604/1 |
| 5,888,199 A | 3/1999 | Karell et al. | |
| 5,897,568 A | 4/1999 | Vanreas | |
| 6,033,417 A | 3/2000 | Tseng | |
| 6,152,940 A * | 11/2000 | Carter | 606/162 |

* cited by examiner

Primary Examiner—Julian W. Woo
Assistant Examiner—Sarah Webb
(74) Attorney, Agent, or Firm—Patents&TMS, P.C.

(57) ABSTRACT

An ear cleaning apparatus, a tip and a method for cleaning an ear are provided. The ear cleaning apparatus may have a tip having protrusions. The protrusions may be made of a pliable material to assist in removing wax, dirt and/or other build-up from within an ear canal. Additionally, the tip may be removable from the apparatus for cleaning and/or replacement.

10 Claims, 1 Drawing Sheet

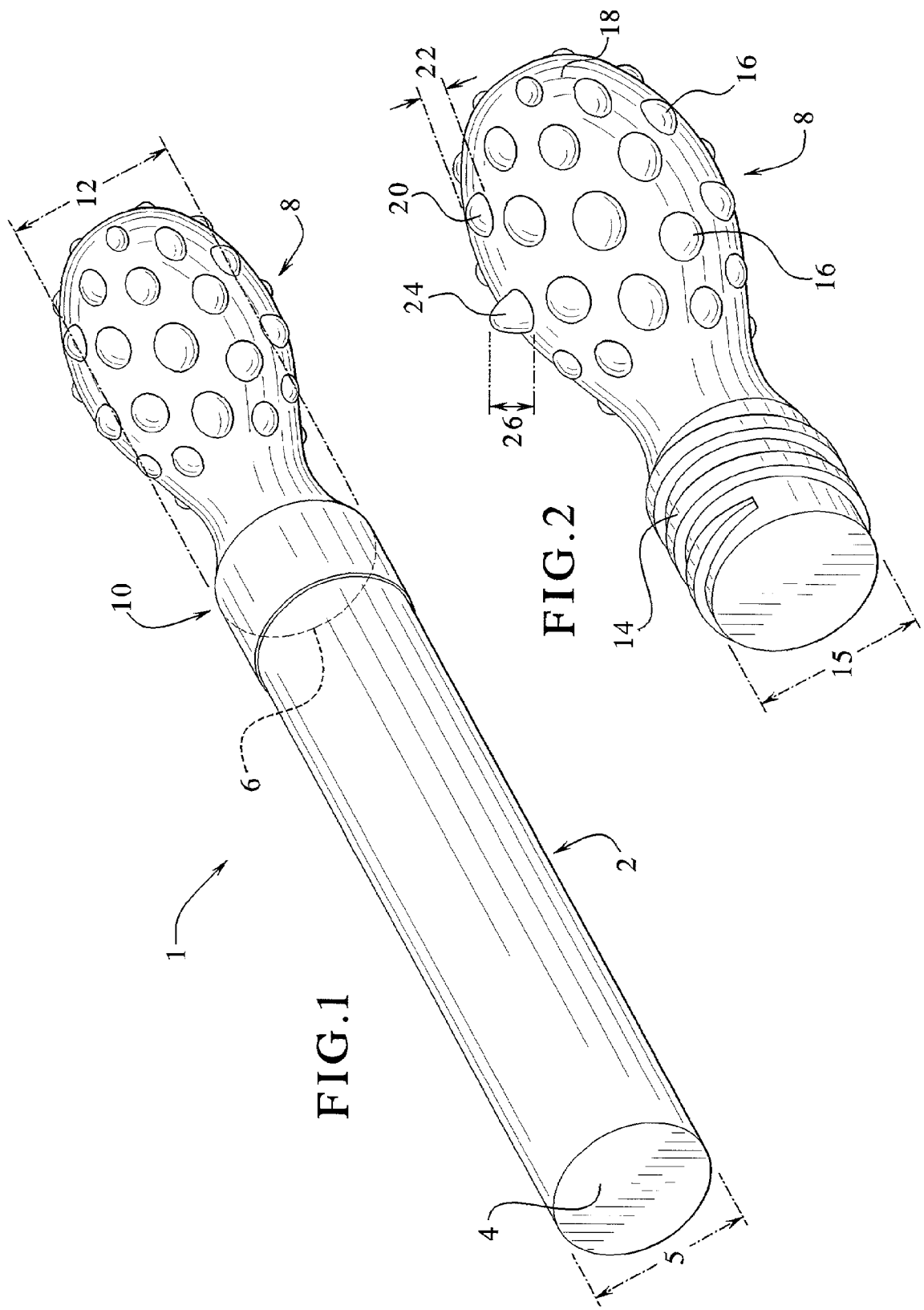

EAR CLEANING APPARATUS, TIP AND A METHOD FOR CLEANING AN EAR

BACKGROUND OF THE INVENTION

The present invention generally relates to an ear cleaning apparatus, tip and a method for cleaning an ear. More specifically, the present invention relates to an ear cleaning apparatus, tip and a method for cleaning an ear wherein the apparatus and tip have protrusions which remove, for example, ear wax, from an ear canal.

Dust and harmful pathogens float in the air. As a result, human ears produce wax as a protective measure against these substances. The wax binds to the dust or pathogens and prevents the dust or pathogens from further entering the body. Over time, the wax build-up may become substantial. If left untreated, wax build-up in an ear canal may adversely affect hearing. Although wax build-up rarely causes deafness, wax build-up should be removed to adequately examine an eardrum.

It is, of course, generally known to provide an ear cleaning apparatus which allows a person to safely clean his/her own ears. The extracting element in known ear cleaning apparatuses is often a paper rod having a wad of cotton attached to one or both ends of the paper rod. The most commonly known ear cleaning apparatus is Q-Tips®, registered trademark of Chesebrough-Pond's, Inc. When the apparatus is rotated, the cotton on the end, or tip, of the rod, creates a frictional surface within the ear which frees and removes wax build-up. Often, the cotton on the tip of the rod is not strong enough to adequately remove the ear wax or dust inside the ear canal. Additionally, multiple rods may be required to clean the ear satisfactorily.

Known ear cleaning apparatuses with cotton on a tip of a rod are usually a one-time disposable apparatus which requires a new apparatus with every use. As a result, daily use of disposable ear cleaning apparatuses may be expensive and environmentally unfriendly as a user may need to replace the cleaning apparatus with each use.

Another problem with cotton ear cleaning apparatuses is that the cotton does not stay on the tip of the rod, either prior to use or during use. In such a case, a person may insert the ear cleaning apparatus into the ear canal and may be injured when the tip of the rod comes into direct contact with the ear drum or other sensitive areas of the ear canal. Additionally, while a person is removing the wax or other build-up with the cotton, the cotton may act as a plunger causing impaction or injury to the ear canal or ear drum.

A need, therefore, exists for an improved apparatus, tip, and a method for cleaning an ear. In addition, a need exists for an apparatus, tip and a method for cleaning an ear wherein the apparatus and tip have protrusions that may be reused and/or replaced.

SUMMARY OF THE INVENTION

The present invention provides an apparatus, tip and a method for cleaning an ear. More specifically, the present invention provides an ear cleaning apparatus having reusable and/or replaceable protrusions on a cleaning end of the apparatus. The cleaning end of the apparatus is reusable to provide multiple usages of the apparatus.

To this end, in an embodiment of the present invention, an ear cleaning apparatus is provided having a body, a tip defined by a periphery and protrusions on the tip extending outside the periphery. The body has a length defined between a first end and a second end. The tip is attached to the first end of the body.

In an embodiment, the tip of the ear cleaning apparatus is removably attached to the first end.

In an embodiment, the ear cleaning apparatus has a threaded connector at the first end of the body.

In an embodiment, the ear cleaning apparatus has a base associated with the tip wherein the base has no protrusions.

In an embodiment, the ear cleaning apparatus has a threaded connector on the tip attached to the body.

In an embodiment, the protrusions on the tip vary in shape.

In an embodiment, the protrusions on the tip vary in size.

In an embodiment, the protrusions are integrally formed with the tip.

In another embodiment of the present invention, a tip is provided having a body and protrusions on the body. The body has an end and the body is defined by a periphery. The protrusions on the body extend outside the periphery.

In an embodiment, the tip has a threaded connector at the end of the body.

In an embodiment, the tip has a base associated with the body wherein the base has no protrusions.

In an embodiment, the protrusions on the tip vary in shape.

In an embodiment, the protrusions on the tip vary in size.

In an embodiment, the protrusions are integrally formed with the tip.

In another embodiment of the present invention, a method for cleaning an ear is provided. The method comprises the steps of: providing a body having a length defined between a first end and a second end; providing a tip defined by a periphery wherein the tip is attached to the first end of the body; providing protrusions on the tip extending outside the periphery; and inserting the tip within an ear canal.

In an embodiment, the method for cleaning an ear further comprises the step of removing the tip from the body.

In an embodiment, the method for cleaning an ear further comprises the step of integrally forming the body with the tip.

In an embodiment, the method for cleaning an ear further comprises the step of integrally forming the tip with the protrusions.

It is, therefore, an advantage of the present invention to provide an ear cleaning apparatus, tip and a method for cleaning an ear that is inexpensive.

Another advantage of the present invention is to provide an ear cleaning apparatus, tip and a method for cleaning an ear that provides an efficient way to remove the build-up of ear wax from the ear canal of an individual.

Another advantage of the present invention is to provide an apparatus, tip and a method for cleaning an ear in a safe way to remove the build-up of ear wax from the ear canal of an individual.

Further, another advantage of the present invention is to provide an apparatus, tip and a method for cleaning an ear wherein the apparatus is reusable.

Still further, another advantage of the present invention is to provide an apparatus, tip and a method for cleaning an ear wherein the apparatus and tip require minimal space.

Another advantage of the present invention is to provide an apparatus, tip and a method for cleaning an ear wherein the apparatus and tip are light weight.

Yet another advantage of the present invention is to provide an apparatus, tip and a method for cleaning an ear wherein the apparatus may be fitted with alternate tips.

Additional features and advantages of the present invention are described in, and will be apparent from, the detailed description of the presently preferred embodiments and from the drawings.

BRIEF DESCRIPTION OF THE DRAWINGS

FIG. 1 is a perspective view of an ear cleaning apparatus in an embodiment of the present invention.

FIG. 2 is a perspective view of a tip of an ear cleaning apparatus in an embodiment of the present invention.

DETAILED DESCRIPTION OF THE PRESENTLY PREFERRED EMBODIMENTS

The present invention generally relates to an ear cleaning apparatus, a tip and a method for cleaning an ear. More specifically, the present invention relates to an ear cleaning apparatus, a tip and a method for cleaning an ear wherein the apparatus and tip have protrusions which remove, for example, ear wax from the ear canal.

Referring now to the drawings wherein like numerals refer to like parts, FIG. 1 generally illustrates an embodiment of an ear cleaning apparatus 1. The apparatus 1 has a body 2 defined by a first end 4, a second end 6 and a diameter 5. The apparatus 1 may also have a tip 8 associated with either the first end 4 and/or the second end 6. FIG. 1 shows the tip 8 attached to the body 2 at the second end 6. The tip 8 may also be associated with the first end 4 of the body 2 (not shown) or both the first end 4 and the second end 6 (not shown).

The body 2, as shown in FIG. 1, may be cylindrical in shape but may be manufactured in a number of different shapes and sizes, such as, for example, rectangular shapes, cylindrical shapes, etc. Further, the body 2, may be constructed from, for example, wood, paper, plastic, or the like.

The tip 8 may have a base 10. Preferably, the base 10 may have a width 12 greater than the diameter 5 of the body 2. The base 10 of the tip 8 may be hollow (not shown) and may fit securely around the diameter 5 of the body 2 as shown in FIG. 1. As further shown in FIG. 1, the base 10 may be cylindrical in shape and may fit securely around the cylindrical shape of the body 2. Of course, the base 10 may be manufactured in a number of different shapes and sizes such as, for example, rectangular shapes, cylindrical shapes, etc. The base 10 of the tip 8 may be constructed in a similar shape of the body 2 to accommodate attachment thereof. Preferably, the base 10 may be integrally formed with the tip 8.

Referring now to FIG. 2, in another embodiment of the present invention, the tip 8 may have a threaded base 14. The threaded base 14 may have a base diameter 15 smaller than the diameter 5 of the body 2. The second end 6 of the body 2 shown in FIG. 1 may be hollow (not shown) and may have threads (not shown) such that the threaded base 14 may be attached and removed from the second end 6 of the body 2. Further, the threaded base 14 may also be attached and removed from the first end 4 of the body 2.

Of course, the tip 8 may be attached to the second end 6 and/or the first end 4 of the body 2 in a number of different ways. Other means for attaching and/or removing the tip 8 from the body 2 are commonly known to those skilled in the art and have not been further described herein. Further, the tip 8 may be integrally formed with the body 2.

Referring again to FIG. 2, the tip 8 may have protrusions 16. The protrusions 16 may extend outward away from a surface 18 of the tip 8. The protrusions 16 may vary in size and shape. For example, a small protrusion 20 may extend outward a small distance 22 from the surface 18 of the tip 8. However, a large protrusion 24 may extend a large distance 26 from the surface 18 of the tip 8.

The protrusions 16 may be constructed from a pliable material, such as, for example, rubber, plastic, cotton, paper, or the like. Further, the protrusions 16 may be constructed with the same material used to construct the tip 8 or may be constructed of a different material than the tip 8. The protrusions 16 may be constructed separately from the tip 8 and attached thereto or may be integrally formed with the tip 8. Further, the protrusions 16 may be individually removed and/or replaced on the tip 8.

To use the ear cleaning apparatus 1 of the present invention, a user may grip the body 2, attached to the tip 8, and insert the tip 8 of the ear cleaning apparatus 1 into, for example, an ear canal (not shown). After the tip 8 of the ear cleaning apparatus 1 is placed inside the ear canal and the tip 8 makes contact with the ear canal, the user may move the body 2. The body 2 may be moved in any direction, such as, for example, in clock-wise/counter-clockwise directions or forward/reverse directions. The movement of the body 2 may allow frictional contact of the protrusions 16 on the tip 8 in the ear canal. The frictional contact of the protrusions 16 in the ear canal may dislodge any wax or dust that may have accumulated within the ear canal.

After the wax or dust is dislodged from the ear canal, the wax or dust may adhere to the protrusions 16 and/or surface 18 of the tip 8. Wax or dust attached to the protrusions 16 and/or surface 18 of the tip 8 may be removed from the ear canal after removal of the tip 8 from the ear canal. Further, the wax or dust may be removed from the protrusions 16 and/or the surface 18 of the tip 8 as needed and the tip 8 may be used again. Alternatively, the user may replace the tip 8 and/or the protrusions 16.

Of course, the ear cleaning apparatus 1 of the present invention may have a number of different uses. For example, the ear cleaning apparatus 1 may be used for the removal of make-up, cleaning jewelry, applying medication to a small wound, and the like.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. An apparatus for cleaning an ear, the apparatus comprising:

a body having a length defined between a first end and a second end;

a tip defined by a first portion and a second portion wherein the first portion has a first length and a first diameter wherein the first diameter is sized to removably attach to the first end of the body and the second portion is integrally formed with the first portion wherein the second portion has a peripheral surface that has a second diameter and a second length wherein the second portion tapers to a smaller diameter as the second portion extends from the first diameter and parabolically increases the diameter of the second portion extending away from the first portion to a maximum diameter greater than the first diameter wherein the diameter of the second portion parabolically decreases from the maximum diameter wherein the second length is greater than the first length and further wherein the second portion of the tip inserts into the ear; and a plurality of protrusions on the second portion of the tip wherein each one of the plurality of protrusions is defined by a boundary that abuts the peripheral surface of the second portion of the tip wherein a first protrusion is adjacent to a second protrusion wherein the boundary of the first protrusion is separated by a first distance from the boundary of the second protrusion and further wherein the second protrusion is adjacent to a third protrusion wherein the boundary of the third protrusion is separated by a second distance from the boundary of the second protrusion wherein the first distance is larger than the second distance and further wherein the plurality of protrusions extend outside of the peripheral surface of the second portion of the tip.

2. The apparatus of claim 1 further comprising:
a threaded connector at the first end of the body.

3. The apparatus of claim 1 further comprising:
a base associated with the tip wherein the base has no protrusions.

4. The apparatus of claim 1 further comprising:
a threaded connector on the tip attached to the body.

5. The apparatus of claim 1 wherein the protrusions on the tip vary in shape.

6. The apparatus of claim 1 wherein the protrusions on the tip vary in size.

7. The apparatus of claim 1 wherein the protrusions are integrally formed with the tip.

8. A method for cleaning an ear, the method comprising the steps of:

providing a body having a length defined between a first end and a second end;

providing a tip wherein the tip has a first portion integrally formed with a second portion wherein the first portion removably attaches to the body and wherein the second portion has a peripheral surface having a length and a diameter greater than the first portion wherein the first portion has a first length and a first diameter and further wherein the second portion has a peripheral surface that has a second diameter and a second length wherein the second portion extends from the first diameter and parabolically increases the diameter of the second portion extending away from the first portion to a maximum diameter greater than the first diameter wherein the diameter of the second portion parabolically decreases from the maximum diameter wherein the second length is greater than the first length;

providing a first protrusion and a plurality of second protrusions on the second portion of the peripheral surface wherein the first protrusion and the plurality of second protrusions have varying heights defined by a distance from the peripheral surface and a distal end of the first protrusion and a distal end of each of the plurality of second protrusions wherein a first distance that the first protrusion extends from the peripheral surface is greater than a second distance that one of the plurality of second protrusions extends from the peripheral surface; and inserting the tip within the ear.

9. The method of claim 8 further comprising the step of:
removing the tip from the body.

10. The method of claim 8 further comprising the step of:
integrally forming the tip with the plurality of second protrusions.

* * * * *